US009192692B2

(12) United States Patent
Medina et al.

(10) Patent No.: US 9,192,692 B2
(45) Date of Patent: *Nov. 24, 2015

(54) CHITOSAN STENTING PASTE (71) Applicant: Medtronic Xomed, Inc., Jacksonville, FL (US)

(72) Inventors: Jennifer Gates Medina, Jacksonville, FL (US); Ethan Glenn Sherman, Jacksonville, FL (US)

(73) Assignee: Medtronic Xomed, INc., Jacksonville, FL (US)

( * ) Notice: Subject to any disclaimer, the term of this patent is extended or adjusted under 35 U.S.C. 154(b) by 160 days.

This patent is subject to a terminal disclaimer.

(21) Appl. No.: 14/061,993

(22) Filed: Oct. 24, 2013

(65) Prior Publication Data
US 2015/0119357 A1  Apr. 30, 2015

(51) Int. Cl.
A01N 43/04     (2006.01)
A61L 24/08     (2006.01)
A61K 31/715    (2006.01)
A61K 31/716    (2006.01)
A61K 31/722    (2006.01)

(52) U.S. Cl.
CPC ............... *A61L 24/08* (2013.01); *A61K 31/715* (2013.01); *A61K 31/716* (2013.01); *A61K 31/722* (2013.01)

(58) Field of Classification Search
None
See application file for complete search history.

(56) References Cited

U.S. PATENT DOCUMENTS

| | | | |
|---|---|---|---|
| 4,394,373 A | 7/1983 | Malette et al. | |
| 4,452,785 A | 6/1984 | Malette et al. | |
| 4,532,134 A | 7/1985 | Malette et al. | |
| 4,572,906 A | 2/1986 | Sparkes et al. | |
| 4,659,700 A | 4/1987 | Jackson | |
| 5,124,151 A | 6/1992 | Viegas et al. | |
| 5,318,780 A | 6/1994 | Viegas et al. | |
| 5,623,064 A | 4/1997 | Vournakis et al. | |
| 5,688,522 A | 11/1997 | Hardy | |
| 5,723,144 A | 3/1998 | Hardy | |
| 5,820,608 A | 10/1998 | Luzio et al. | |
| 5,871,985 A | 2/1999 | Aebischer et al. | |
| 5,902,798 A | 5/1999 | Gouda et al. | |
| 5,958,443 A | 9/1999 | Viegas et al. | |
| 6,096,018 A | 8/2000 | Luzio et al. | |
| 6,344,077 B1 | 2/2002 | Hong | |
| 6,344,488 B1 | 2/2002 | Chenite et al. | |
| 6,458,375 B1 | 10/2002 | Gertzman et al. | |
| RE38,431 E | 2/2004 | Miekka et al. | |
| 7,098,194 B2 | 8/2006 | Chenite et al. | |
| 7,148,209 B2 | 12/2006 | Hoemann et al. | |
| 7,195,675 B2 | 3/2007 | Okazaki et al. | |
| 7,307,157 B2 | 12/2007 | Yoshii et al. | |
| 7,959,943 B2 | 6/2011 | Hissong et al. | |
| 7,968,122 B2 | 6/2011 | Chen | |
| 7,976,873 B2 | 7/2011 | Myntti et al. | |
| 7,976,875 B2 | 7/2011 | Myntti | |
| 8,034,371 B2 | 10/2011 | Castile et al. | |
| 8,153,612 B2 | 4/2012 | Ben-Shalom et al. | |
| 8,357,787 B2 | 1/2013 | Nichols et al. | |
| 8,361,504 B2 | 1/2013 | Hen et al. | |
| 8,383,157 B2 | 2/2013 | Muzzarelli et al. | |
| 8,389,467 B2 | 3/2013 | Chaput et al. | |
| 8,431,160 B2 | 4/2013 | O'Hagen et al. | |
| 8,470,346 B2 | 6/2013 | Chen | |
| 8,470,369 B2 | 6/2013 | Marchosky | |
| 8,506,972 B2 | 8/2013 | Chenite et al. | |
| 8,536,230 B2 | 9/2013 | Laurencin et al. | |
| 8,653,319 B2 | 2/2014 | Amery et al. | |
| 2002/0058704 A1 | 5/2002 | Malik | |
| 2003/0143274 A1* | 7/2003 | Viegas et al. | 424/486 |
| 2005/0042265 A1 | 2/2005 | Guillot et al. | |
| 2005/0136122 A1 | 6/2005 | Sadozai et al. | |
| 2006/0127873 A1 | 6/2006 | Hoemann et al. | |
| 2006/0172000 A1 | 8/2006 | Cullen et al. | |
| 2006/0287278 A1 | 12/2006 | Hu et al. | |
| 2008/0248991 A1 | 10/2008 | Dyer et al. | |
| 2009/0022770 A1 | 1/2009 | Andersson | |
| 2009/0202430 A1 | 8/2009 | Hoemann et al. | |
| 2009/0269417 A1 | 10/2009 | Gonzalez et al. | |
| 2009/0270514 A1 | 10/2009 | Laurencin et al. | |
| 2009/0291911 A1 | 11/2009 | Myntti et al. | |
| 2009/0291912 A1 | 11/2009 | Tijsma et al. | |
| 2010/0172953 A1 | 7/2010 | Larsen et al. | |
| 2010/0316715 A1 | 12/2010 | Andersson | |
| 2011/0040226 A1 | 2/2011 | Amery et al. | |
| 2011/0245757 A1 | 10/2011 | Myntti et al. | |

(Continued)

FOREIGN PATENT DOCUMENTS

| | | |
|---|---|---|
| EP | 0 329 098 B1 | 5/1994 |
| EP | 1 190 702 A1 | 3/2002 |
| WO | WO 96/13284 | 5/1996 |
| WO | WO 99/07416 | 2/1999 |
| WO | WO 02/40072 | 5/2002 |
| WO | 03020771 A1 | 3/2003 |
| WO | WO 2010/033943 A1 | 3/2010 |
| WO | WO 2011/060545 A1 | 5/2011 |

OTHER PUBLICATIONS

Schaffhausen et al. Abstracts/Journal of Controlled Release (2008), vol. 132, pp. e47-e48.*

(Continued)

*Primary Examiner* — Patrick Lewis
(74) *Attorney, Agent, or Firm* — IPLM Group, P.A.

(57) ABSTRACT

Nasal or sinus site may be treated with a ready-to-use paste having a high concentration of a water-soluble chitosan, an osmolality reducing agent in a phosphate-containing solution. The paste forms at room temperature, has a pH of at least 4 and the osmolality reducing agent does not crosslink with the water-soluble chitosan. The paste provides stenting and adheres to the nasal or sinus site and has a residence time of at least 1 day.

20 Claims, 1 Drawing Sheet

(56) References Cited

U.S. PATENT DOCUMENTS

2011/0313056 A1  12/2011  Buschmann et al.
2012/0052012 A1  3/2012   Chenite et al.
2012/0329751 A1  12/2012  Baker et al.
2013/0004474 A1  1/2013   Ouyang et al.

OTHER PUBLICATIONS

Ahmadi et al. Journal of Tissue Engineering and Regenerative Medicine (2010), vol. 4, pp. 309-315.*
Roldo et al., "Mucoadhesive thiolated chitosans as platforms for oral controlled drug delivery: synthesis and in vitro evaluation", European Journal of Pharmaceutics and Biopharmaceutics, 57, 115-121 (2004).
Krauland et al., "Viscoelastic Properties of a New in situ Gelling Thiolated Chitosan Conjugate", Drug Development and Industrial Pharmacy, 31, 885-893 (2005).
Bernkop-Schnürch, "Thiomers: A new generation of mucoadhesive polymers", Advanced Drug Delivery Reviews, 57, 1569-1582 (2005).
Bernkop-Schnürch et al., "Thiomers: Preparation and in vitro evaluation of a mucoadhesive nanoparticulate drug delivery system", International Journal of Pharmaceutics, 317, 76-81 (2006).
Ambrose et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds", Antimicrobial Agents and Chemotherapy, vol. 36, No. 9, 1799-1803 (Sep. 1991).
Bernkop-Schnürch et al., "Thiolated polymers—thiomers: synthesis and in vitro evaluation of chitosan-2-iminothiolane conjugates", International Journal of Pharmaceutics, 260, 229-237 (2003).
Kumar, R. M.N.V. et al., Chitosan Chemistry and Pharmaceutical Perspectives, Chem. Rev., 104, pp. 6017-6084 (2004).
Chelladurai S, et al., Design and Evaluation of Bioadhesive in-Situ Nasal Gel of Ketorolac Tromethamine, Chem. Pharm. Bull. 56(11), pp. 1596-1599 (2008).
Ahmadi, R. et al., Biocompatibility and gelation of chitosan-glycerol phosphate hydrogels, Journal of Biomedical Materials Research Part A, 10 pages (2007).
Athanasiadis, T. MBBS et al., Effects of a Novel Chitosan Gel on Mucosal Wound Healing Following Endoscopic Sinue Surgery in a Sheep Model of Chronic Rhinosinusitus, The Laryngoscope, 118, 1088-1094 (2008).
Ling L. et al., Biodegradable and injectable in situ cross-linking chitosan-hyaluronic acid based hydrogels for postoperative adhesion prevention, Biomaterials, 35, pp. 3903-3917 (2014).
Aziz M.A. et al., In vitro biocompatibility and cellular interactions of a chitosan/dextran-based hydrogel for postsurgical adhesion prevention, J Biomed Mater Res. Part B, 103B, pp. 332-341 (2014).
Kourelis K. et al., Effectiveness of chitosan-based packing in 35 patients with recalcitrant epistaxis in the context of coagulopathy, Clinical Otolaryngology, 37(4), pp. 305-330 (2012).
Shikani A.H. et al., Endoscopically guided chitosan nasal packing for intractable epistaxis, American Journal of Rhinology & Allergy, 25(1), pp. 61-63 (2011).
Ha et al., A blinded randomized controlled trial evaluating the efficacy of chitosan gel on ostial stenosis following endoscopic sinus surgery, International Forum of Allergy and Rhinology, vol. 3, No. 7, pp. 573-580 (2013).
Rao S.B. et al., Use of chitosan as a biomaterial: studies on its safety and hemostatic potential, Journal of Biomedical Materials Research, vol. 34, pp. 21-28 (1997).
Malette W.G. M.D. et al., Chitosan: A New Hemostatic Ann Thorac Surg., 36, pp. 55-58 (1983).
Chou T.C. et al., Chitosan enhances platelet adhesion and aggregation, Biochemical and Biophysical Research Communications,302, pp. 480-483 (2003).
Dutkiewicz J.K., Superabsorbent Materials from Shellfish Waste—A Review, J Biomed Mater Res., 63, pp. 373-381(2002).
Brandenberg G. B.S., Chitosan: A New Topical Hemostatic Agent for Diffuse Capillary Bleeding in Brain Tissue, Department of Neurosurgery, Pathology, and Surgery, University of Nebraska Medical Center and Omaha Veterans Administration Medical Center, vol. 15, No. 1, pp. 9-13 (1984).
Hirano S. et al., Wet spun chitosan-collagen fibers, their chemical N-modifications, and blood compatibility, Biomaterials, 21, pp. 997-1003 (2000).
Belman A. M.D. et al., From the Battlefield to the Street—Experience of a Suburban Fire/EMS Agency with Chitosan Dressing, Emergency Medicine & Critical Care Review (2006).
Wedmore I. M.D. et al., A Special Report on the Chitosan-based Hemostatic Dressing: Experience in Current Combat Operations, Journal of Trauma, vol. 60, No. 3, pp. 655-658 (2006).

* cited by examiner

CHITOSAN STENTING PASTE

FIELD OF THE INVENTION

This invention relates to biomaterials for use in or on tissue and structures in the throat, nasal passages and elsewhere in or near the respiratory tract.

BACKGROUND

Sinusitis is an inflammation of the mucosal tissue lining of the sinus walls which may lead to nasal passageway blockage, mucous stagnation and bacterial or fungal sinus cavity infection. Typical treatments begin with antibiotics. However, when antibiotics cannot relieve sinusitis, sinus surgery (which involves opening the sinus cavities and removing mucosal tissue) may be an alternative. Post-operative care for such surgery requires temporary and uncomfortable sinus packing or gauze which supports the reopened sinus passage and absorbs excess fluid while the tissues heal. After several days or at the discretion of the physician, the gauze packing is removed. Doing so is painful.

SUMMARY OF THE INVENTION

Sinus sealants and other biological materials have emerged as a promising technique to temporarily seal, stent or otherwise protect post-operative sinus passageways with less intrusion and pain than traditional packing techniques.

Packing or biomaterial stents that dissolve or otherwise degrade over a certain period are desirable. The packing or stents desirably should be able to be dispensed through a suitable dispensing device (for example, a syringe) using a single, gloved hand. Packing or stents should also desirably be provided as ready-to-use injectable or extrudable compositions.

The present invention provides, in one aspect, a sinus stent paste comprising a water-soluble chitosan or derivative thereof and an osmolality reducing agent in a phosphate-containing solution to provide a paste at room temperature, having a pH of at least 4, a viscosity of about 1 to about 15 Pa·s., an osmolality of about 270 to about 2000 mOsm/kg, a residence time of at least 1 day, wherein the osmolality reducing agent does not crosslink with the water-soluble chitosan.

The present invention provides, in another aspect, a method of preparing a chitosan stenting paste comprising the steps of:

mixing a water-soluble chitosan or derivative thereof and an osmolality reducing agent in a phosphate-containing solution to provide a paste at room temperature, having a pH of at least 4, a viscosity of about 1 to about 15 Pa·s., an osmolality of about 270 to about 2000 mOsm/kg, a residence time of at least 1 day, wherein the osmolality reducing agent does not crosslink with the water-soluble chitosan.

The invention also provides in yet another aspect, a method of stenting comprising:

a) providing a composition comprising a water-soluble chitosan or derivative thereof and an osmolality reducing agent in a phosphate-containing solution to provide a paste at room temperature, having a pH of at least 4, a viscosity of about 1 to about 15 Pa·s., an osmolality of about 270 to about 2000 mOsm/kg, wherein the osmolality reducing agent does not crosslink with the water-soluble chitosan; and b) applying the paste onto a nasal or sinus site to form a protective packing, layer or stent wherein the paste adheres to the nasal or sinus site and has a residence time of at least 1 day.

The disclosed paste, stent and method are especially useful for nasal and sinus surgery.

BRIEF DESCRIPTION OF THE DRAWING

Like reference symbols in the various figures of the drawing indicate like elements. The elements in the drawing are not to scale.

DETAILED DESCRIPTION

The following detailed description describes certain embodiments and is not to be taken in a limiting sense. All weights, amounts and ratios herein are by weight, unless otherwise specifically noted. The terms shown below have the following meanings:

The term "adhesion" refers to the sticking together of a body structure or prosthetic material to tissue, to the sticking together of tissue to tissue with which it is in intimate contact for an extended period, or to the formation of tissue that connects body structures, prosthetic materials or tissues to one another across a normally open space.

The term "antimicrobial" when used in reference to a substance means that the substance can kill, significantly inhibit or control the growth of microbes, for example bacteria such as *Staphylococcus aureus, Streptococcus epidermis, Pseudomonas aeruginosa* or *Escherichia coli.*

The term "biocompatible" when used in reference to a substance means that the substance presents no significant deleterious or untoward effects upon the body.

The term "biodegradable" when used in reference to a substance means that the substance will degrade or erode in vivo to form smaller chemical or physical species. Such degradation process may be enzymatic, chemical or physical.

The term "chitosan" refers to a polysaccharide polymer containing randomly distributed β-(1-4)-linked D-glucosamine (deacetylated) and optional N-acetyl-D-glucosamine (acetylated) monomer units, and includes chitosan derivatives in which one or more hydroxyl or amine groups of the polymer have been modified to alter the solubility or mucoadhesion characteristics of the derivative.

The term "conformal" when used in reference to a paste applied to tissue or other body structure means that the paste can form a substantially continuous layer over an area to which the paste has been applied.

The term "hemostat" means a device or material which stops blood flow.

The term "mucoadhesive" when used in reference to a substance means that the substance will adhere to the mucus covering epithelia.

The term "nasal or sinus" refers to the various tissues defining the normally air-filled passages and chambers within the nose and sinus cavities including but not limited to the nostrils or nares, the nasal concha or turbinates, the frontal, ethmoid, sphenoid and maxillary sinuses, the sinus ostia and the nasopharnyx.

The term "opaque" when used in reference to a material means that ordinary overhead illumination is not transmitted through about a 4 mm thick layer of the material.

The term "osmolality" means the number of osmoles of solute per kilogram of solvent, as measured using a freezing point depression osmometer.

The term "paste" when used in reference to a substance means the substance is a visibly homogenous, nonporous, opaque material having a soft, malleable, spreadable consistency, for example similar to toothpaste, and a viscosity such that the material is suitable for use in stenting (e.g. holding apart) nasal or sinus tissue. An opaque gel may be a paste. A collection of free flowing dry solid particles, a non-malleable solid, a porous sponge, a translucent gel, a liquid or a sprayable composition would not be a paste.

The term "protective" when used in reference to a paste applied to tissue or other body structure means that the paste may assist in returning an injured, inflamed or surgically repaired tissue surface to a normal state, e.g., through one or more healing mechanisms such as modulation of an inflammatory response, phagocytosis, mucosal remodeling, reciliation or other full or partial restoration of normal function.

The term "residence time" when used in reference to a paste applied to tissue or other body structure means the time period during which the paste or portion thereof remains in place in vivo under gross observation.

The term "thin" when used in reference to a protective layer atop tissue or other body structure means having an average thickness less than about five millimeters.

The term "tonicity" when used in reference to a cell's response (e.g. ciliated tissue such as found in the ear, nose and throat) to an external substance refers to the sum of the concentration of solutes having the capacity to exert an osmotic force across a given membrane. Solutes that cannot cross the cell membrane exert an osmotic force. Depending on the solute concentration of the substance in reference to the cell membrane, tonicity may be referred to as "hypertonic", "hypotonic" or "isotonic". "Hypertonic" refers to a substance with a higher solute concentration outside a cell membrane. As such, when the substance contacts the cell membrane, water in the cell will have a tendency to move out of the cell to balance the solute concentration outside the cell membrane. "Hypotonic" refers to substance with a lower solute concentration outside the cell membrane. As such, water from outside the cell will enter into the cell, causing swelling in an attempt to balance the solute concentration inside the cell. "Isotonic" refers to a substance's solute concentration that is the same as the cell to which it comes in contact. As such, it is considered physiological with the cell and hence there is no net flow of water.

The term "viscosity" when used in reference to a substance is the extent to which the substance resists a tendency to flow when subjected to stress. Viscosity may be measured with a cone and plate viscometer that imposes a specific stress on the substance and the resultant stress deformation or resistance is measured according to ASTM F2103-11 (Part 5). The units of viscosity are reported as Pascal-seconds (Pa·s.). For the disclosed pastes, viscosity values are determined and reported after the paste has been sterilized.

The disclosed paste or method includes a high concentration of a water-soluble chitosan (e.g. chitosan salt) and an osmolality reducing agent in a phosphate-containing solution, the paste having a pH of at least 4. The disclosed paste desirably has an off white to yellowish coloration, which makes it easy to visualize when applied. The disclosed paste may also be desirably opaque. The disclosed paste is also desirably provided in a ready-to-use, storage-stable, injectable or extrudable form, requiring no or minimal preparation. The osmolality reducing agent is desirably not a chitosan nor is the osmolality reducing agent crosslinkable with the chitosan. Because the paste desirably does not include crosslinkers, it can be stored for extended periods of time and desirably does not require further hydration or other similar preparation steps before application.

The disclosed paste may be prepared by mixing or dissolving the initially solid ingredients (e.g., water-soluble chitosan and an osmolality reducing agent) in a phosphate containing solution (e.g., phosphate buffered saline (PBS)). A paste is formed at room temperature (e.g. about 20° C. to about 25° C.) when the ingredients become solubilized and remains a paste at room temperature.

Figure 1:
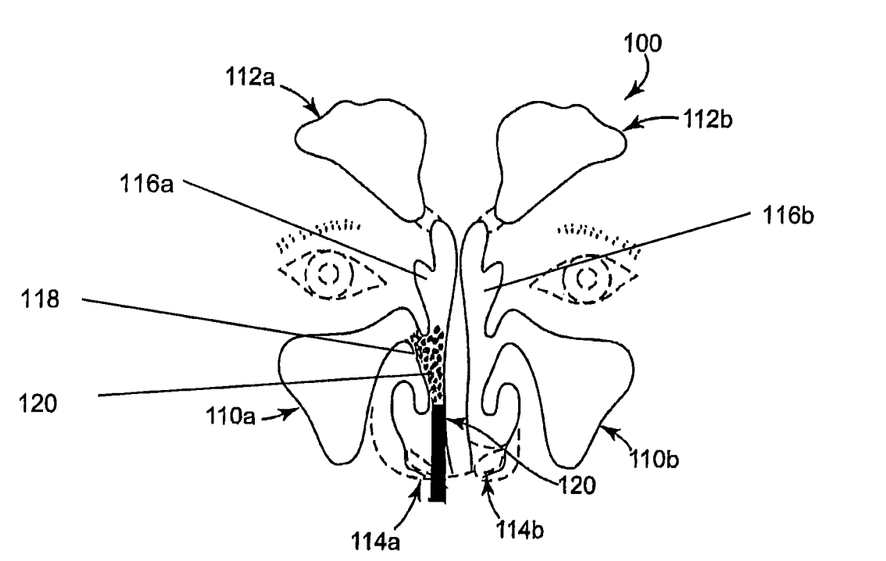
FIG. 1 is a schematic view showing application of the disclosed paste to stent the middle turbinate.

Referring to FIG. 1, the disclosed paste or method may be used or performed for example in the nasal or sinus cavities 100 of a patient, including the maxillary sinuses 110a, 110b, frontal sinuses 112a, 112b, which may be accessed through nares 114a, 114b and turbinates 116a, 116b. It should be noted that external features of the patient, including nares 114a, 114b, are shown in dashed lines. When the patient suffers for example from chronic rhinosinusitis, one or more treatment sites such as treatment site 118 associated with the middle turbinate 116 may be medically or if need be surgically addressed. A layer 120 of the disclosed paste may be applied to site 118 and allowed to remain in place while healing takes place.

Those skilled in the art will appreciate that the disclosed paste may be applied in or to other body parts. The disclosed paste may for example have utility in vascular or non-vascular applications, including treatment of tissues (e.g., mucosal tissues) or other tissues or structures in or near the ears, throat, limbs or spinal column.

The applied paste may fill the treatment site (e.g., a nasal or sinus cavity, or an opening, recess, passageway or joint in a portion of the limbs or spinal column), in which case the disclosed paste may be very thick and not exposed to air or other nearby gases, and with differing thicknesses throughout. The disclosed paste may also be applied as a thin film or other conformal coating in which case the layer may be relatively thin and exposed to air or other nearby gases, and with a substantially uniform thickness throughout the layer. The protective paste desirably adheres to mucosal or other natural tissues (e.g., cartilage or bone) at the treatment site and resists detachment or other disruption until natural degradation or degradation initiated by irrigation or hydrolysis takes place, e.g., after a residence time in vivo from at least 1 day, at least 3 days, at least 5 days, at least 7 days, at least 15 days, up to about 3 weeks, up to about 4 weeks, up to about 45 days or up to about 60 days. Meanwhile bacterial recolonization or reinfection may be significantly reduced or prevented, and improved healing (e.g. reciliation) may take place. The protective paste may provide various therapeutic advantages including but not limited to bacterial adhesion repellence, anti-infective properties, local immune modulation, tissue protection, reduction or elimination of pain or bleeding, reduction in inflammation, optimization of environment for ciliary regrowth, reduction in adhesions to critical anatomy, and the like. These advantages may arise due to a variety of mechanisms including a) killing bacteria, b) inhibiting bacterial colonization, c) inhibiting the adherence of bacteria to tissue, d) reducing tissue morbidity or abscess formation, e) reducing or preventing disease recurrence (for example, specifically reducing the chronic inflammation related to bacterial toxins, biofilm or extracellular polymeric substance toxins, f) coating and protecting tissue during healing, such as by maintenance of a moist wound which promotes platelet aggregation, or by closure of a dry wound without excessive scabrous formation, g) hemostasis, h) optimizing the environment for reciliation of the mucosa, i) speeding the growth or regrowth of cilia and j) delivering therapeutic agent(s) to the treatment site.

Desirably the protective paste will adhere to a portion of the mucosa while leaving the cilia in unadhered portions free to undergo natural rhythmic cilia motion (viz., cilia beating), if desired also will deliver antimicrobial agents or additional therapeutic agents, and desirably will discourage or prevent bacteria from colonizing on the treatment site.

Water-soluble chitosans, preferably chitosan salts may be used to form the paste. For example, high concentrations of a chitosan salt may be mixed in a phosphate-containing solution (e.g. PBS, glycerol phosphate disodium salt hydrate or any combination thereof) to provide a ready-to use paste. The paste may be opaque because of the high chitosan concentration or after sterilization. Without intending to be bound by theory, the phosphates and chitosan may react via an ionic reaction to help form the paste. Exemplary chitosan concentrations may be from about 3 to about 20 wt. %, about 5 to about 8 wt. %, about 8 wt. % to about 12 wt. %, about 12 wt. % to about 18 wt. %, about 16 wt. % to about 18 wt. % or about 18 wt. % to about 20 wt. % of the total paste weight. The high chitosan concentrations used in the paste result in viscosities desirable for good stenting and acceptable syringe delivery force. Desired viscosities range from about 1 to about 15 Pa·s. when tested at 25° C. and a shear rate of 221 $s^{-1}$. This shear rate correlates to the approximate average shear rate the substance may experience as it is dispensed through a standard 30 ml BD™ syringe with a LUER LOCK™ connector at a rate of 1 ml/s.

Exemplary unmodified, water-soluble chitosans and their salts (including chloride, citrate, nitrate, lactate, phosphate, and glutamate salts) may be obtained from a variety of commercial sources including sources described in US Patent Application Publication No. 2009/0291911.

Chitosan may also be synthesized by deacetylation of chitin (poly-N-acetyl-D-glucosamine) to eliminate acetyl groups on the nitrogen atom by hydrolysis. The resulting polymer has a plurality of repeating units (e.g., about 30 to about 3000 repeating units, about 60 to about 600 repeating units, or such other amount as may be desired for the chosen end use) some or all of which contain deacetylated amino groups (e.g., about 30 to about 100% or about 60 to about 95% of the total repeating units), with the remaining repeating units (if any) containing acetylated amino groups. The polymer is cationic and may be regarded as being composed from glucosamine monomers.

The chitosan may have a variety of number average molecular weights, e.g., about 5 to about 2000 kDa, about 10 to about 500 kDa, or about 10 to about 100 kDa. The chitosan may for example be an ultralow molecular weight material having a number average molecular weight less than or about 30 kDa, a low molecular weight material having a number average molecular weight of about 30 to about 400 kDa, a medium molecular weight material having a number average molecular weight of about 200 to about 500 kDa or a high molecular weight material having a number average molecular weight greater than or about 500 kDa. A low molecular weight chitosan is preferred. The disclosed molecular weights are weights before sterilization of the paste. The chitosan desirably is in dry particulate form, for example, as free-flowing granules whose average particle diameter is less than or about 1 mm, less than or about 100 µm, or about 1 to about 80 µm, or less than 1 µm.

Chitosan derivatives may also be employed, for example derivatives in which one or more hydroxyl or amino groups have been modified for the purpose of altering the solubility or mucoadhesion characteristics of the derivative. Exemplary derivatives include thiolated chitosans, and non-thiolated chitosan derivatives such as acetylated, alkylated or sulfonated chitosans (for example O-alkyl ethers, O-acyl esters, cationized trimethyl chitosans and chitosans modified with polyethylene glycol). Chitosan derivatives may be obtained from a variety of sources. For example, thiolated chitosans may be obtained from ThioMatrix Forschungs Beratungs GmbH and Mucobiomer Biotechnologische Forschungs-und Entwicklungs GmbH or prepared by reaction of chitosan with a suitable thiolated reactant, e.g., as described in Published PCT Application No. WO 03/020771 in Roldo et al., *Mucoadhesive thiolated chitosans as platforms for oral controlled drug delivery: synthesis and in vitro evaluation*, European Journal of Pharmaceutics and Biopharmaceutics, 57, 115-121 (2004); Krauland et al., *Viscoelastic Properties of a New in situ Gelling Thiolated Chitosan Conjugate*, Drug Development And Industrial Pharmacy, 31, 885-893 (2005); Bernkop-Schnürch, *Thiomers: A new generation of mucoadhesive polymers*, Advanced Drug Delivery Reviews, 57, 1569-1582 (2005); and Bernkop-Schnürch et al., *Thiomers: Preparation and in vitro evaluation of a mucoadhesive nanoparticulate drug delivery system*, International journal of Pharmaceutics, 317, 76-81 (2006).

While a high chitosan concentration has a desired viscosity for stenting, it also results in high osmolality (e.g. a paste made from about 18 wt % chitosan HCl and having a molecular weight in the range of about 30 to about 400 kDa results in an osmolality of about 2800 mOsm/kg). A high osmolality paste may not be physiologically compatible with the cells or tissues to which the paste may be applied. Desired osmolality is such that the paste is considered isotonic or hypertonic to the cells or tissues (e.g. ciliated tissue) to which the paste is applied. It is preferable that the paste have an osmolality of less than about 2000 mOsm/kg, for example from about 270 to about 2000 mOsm/kg or about 270 to about 1500 mOsm/kg, yet has a desirable viscosity.

To maintain or lower the osmolality without significantly altering or reducing the desired viscosity or the paste-like consistency, it was found that one or more osmolality reducing agents may be used. Recommended amounts of the osmolality reducing agent may for example be about 1 to about 20 wt. %, about 1 to about 10 wt. % or about 2 to about 8% wt. of the total paste weight. Examples of suitable osmolality reducing agents include polysaccharides other than chitosans that are biocompatible and which reduce osmolality in the disclosed paste but which do not crosslink the chitosan. Examples of such polysaccharides include agars, alginates, carrageenans, celluloses, dextrans, galactomannans, glycogens, hyaluronic acids, and starches.

Preferred polysaccharides include hydroxyl functional or alkyl modified celluloses. Exemplary cellulose materials include methylcellulose, ethylcellulose, hydroxybutyl methylcellulose, hydroxyethylcellulose, hydroxypropylcellulose, hydroxypropyl methylcellulose, carboxymethylcellulose, and mixtures thereof. Without intending to be bound by theory, it is believed that the osmolality reducing agent serves as a "salt scavenger" that may help reduce the paste's osmolality and maintain the desired paste-like consistency.

The paste may for example contain chitosan and an osmolality reducing agent in a combined amount representing about 1 to about 20 wt. %, about 10 to about 20 wt. % or about 10 to about 15 wt % of the total paste composition. The chitosan and osmolality reducing agent may for example be combined in a ratio of about 10:1 to about 1:20, about 5:1 to about 1:10, or about 3:1 to about 1:5.

The paste desirably has a pH appropriate for contacting human tissue, e.g., a pH of at least 4, a near-neutral pH, or a pH less than 10. An acid, base or buffering agent may for example be included to help maintain an appropriate pH. Buffering agents are preferred and phosphate-containing buffers are most preferred. Exemplary buffering agents include mixtures of barbitone sodium, glycinamide, glycine, potassium chloride, potassium phosphate, potassium hydrogen phthalate, sodium acetate, sodium citrate or sodium phosphate with their conjugate acids (for example a mixture of sodium citrate and citric acid).

Exemplary phosphate-containing buffers are derived from phosphoric acid and a base selected from potassium hydroxide, sodium hydroxide, the potassium or sodium salts of phosphoric acid, mixtures thereof and the like. Exemplary phosphate salts include sodium phosphate dibasic and monobasic, potassium phosphate dibasic and monobasic and mixtures thereof. The concentration of phosphoric acid and base or salt in the disclosed buffering agent may be varied to achieve the desired pH.

As discussed above, the chitosan and the osmolality reducing agent are desirably dissolved in the phosphate-containing solution. Exemplary phosphate-containing solutions include phosphate-containing buffers such as PBS. PBS solutions typically include a combination of one or more phosphate salts and one or more chloride salts. Exemplary phosphate salts include disodium phosphate, potassium dihydrogen phosphate or a combination thereof. Exemplary chloride salts include sodium chloride, potassium chloride or a combination thereof. The salts used to prepare the PBS solution are optionally hydrates. An exemplary combination of salts employs disodium phosphate heptahydrate ($Na_2HPO_4.7H_2O$) and potassium dihydrogen phosphate ($KH_2PO_4$), in a so-called 1X PBS solution with concentrations of about 0.01M phosphate, about 0.0027M KCl, about 0.137 M NaCl and a pH of 7.4 at 25° C. PBS buffer solutions may be prepared in other strengths such as 2×, 3×, 5×, 10× or any other suitable strength. For example, a 10X PBS buffer may be prepared by adding 10 times the ingredients described for a 1X PBS buffer to result in concentrations of about 0.1M phosphate, about 0.027M KCl, about 1.37 M NaCl. The PBS buffer desirably has a pH between about 9 to about 12. Preferably, the PBS solution is a 3× solution having a pH of about 11.

Phosphates may also be provided as salts of glycerol-3-phosphate (GlyPhos) (e.g., as sodium, potassium, calcium or magnesium salts). Stereoisomeric forms of GlyPhos, preferably the racemic, meso, α and β blends or other forms or blends, may also be used. In some embodiments, the phosphate may be provided by the buffering agent (e.g. PBS), by a salt of GlyPhos or both. Preferably, the phosphate-containing solution is a PBS solution and most preferably is greater than a 1×PBS solution.

Lubricants and wetting agents may also be included to help maintain paste consistency. In addition, lubricants and wetting agents may aid in dispensing the paste into or onto a desired treatment site. Desirably, the paste should be able to be dispensed by an operator from a suitable delivery device (for example a syringe) using a single gloved hand. One preferred class of lubricants and wetting agents includes hydroxy compounds having two or more hydroxyl groups with the presence of 1,2-diol grouping being desirable. Hydroxy compounds having 2-4 carbon atoms have been found to be particularly useful lubricants. Glycerol is especially preferred. Other compounds include ethane-1,2-diol; propane-1,2-diol; butane-1,3-diol and butane-1,4-diol. Mixtures of hydroxy compounds may be employed, especially mixtures of glycerol and one or more diols. Desired amounts of the lubricants and wetting agents may for example be about 1 to about 15 wt % or about 2 to about 12 wt % of the total paste weight.

Exemplary therapeutic agents which may be employed in the disclosed paste include any material suitable for use at the intended treatment site including analgesics, anti-cholinergics, anti-fungal agents, antihistamines, steroidal or non-steroidal anti-inflammatory agents, anti-parasitic agents, antiviral agents, biostatic paste, chemotherapeutic agents, antineoplastic agents, cytokines, decongestants, hemostatic agents (e.g., thrombin), immunosuppressors, mucolytics, nucleic acids, peptides, proteins, steroids, vasoconstrictors, vitamins, mixtures thereof, and other therapeutic materials that will be known to those skilled in the art. A useful list of such therapeutic agents may also be found, for example, in U.S. Pat. No. 7,959,943.

The disclosed paste desirably is inherently antimicrobial without requiring addition of a separate antimicrobial agent. Antimicrobial activity may be influenced by the proportion of chitosan in the paste. A separate antimicrobial agent may be employed if desired. A useful list of such antimicrobial agents may be found, for example, in U.S. Pat. No. 7,959,943.

Other adjuvants that may be included in the disclosed paste include dyes, pigments or other colorants (e.g., FD & C Red No. 3, FD & C Red No. 20, FD & C Yellow No. 6, FD & C Blue No. 2, D & C Green No. 5, D & C Orange No. 4, D & C Red No. 8, caramel, titanium dioxide, fruit or vegetable colorants such as beet powder or beta-carotene, turmeric, paprika and other materials that will be known to those skilled in the art); indicators; flavoring or sweetening agents including but not limited to anise oil, cherry, cinnamon oil, citrus oil (e.g., lemon, lime or orange oil), cocoa, eucalyptus, herbal aromatics (e.g., clove oil, sage oil or cassia oil), lactose, maltose, menthol, peppermint oil, saccharine, sodium cyclamate, spearmint oil, sorbitol, sucrose, vanillin, wintergreen oil, xylitol and mixtures thereof; antioxidants; antifoam agents; and thixotropes. Where sustained release or delayed release of a therapeutic agent is desirable, a release agent modifier may also be included.

The disclosed paste typically will be placed in suitable sealed packaging (for example, a syringe, a vial, or pouch made of suitable materials) and subjected to sterilization. Sterilization methods that do not unduly discolor (e.g. brown), affect the adhesive strength, viscosity or otherwise unduly affect the paste's consistency are desirable. Suitable sterilization methods include steam or ionizing radiation (e.g. gamma radiation or electron beam (E-Beam)). E-Beam sterilization appears to prevent or limit paste discoloration. E-beam sterilization may be performed at reduced temperatures as described in U.S. Patent Application Publication No. US 2001/0040226 A1 (Amery et al). E-beam or gamma sterilization may for example be used at doses in the range of about 12 to about 40 kGy. The disclosed paste may be opaque after sterilization.

The paste desirably is provided as a ready-to-use composition requiring little or no preparation. The paste desirably is in a form that is injectable or extrudable. The paste desirably has good shelf life as determined by adhesive force, viscosity and pH, and preferably may be stored for more than 12 months. For example, the paste may be stored for more than 15 months, more than 18 months or up to 24 months. If the paste appears to have separated, re-mixing (e.g. back and forth between two syringes) returns the paste to more homogenous consistency. However, the paste preferably does not separate during storage. The paste is desirably stable at temperatures ranging from 2° C. to about 60° C. In addition, the paste desirably remains a paste after exposure to extreme temperature ranges imposed during ISTA-2A testing (e.g., about −29° C. to about 60° C.).

The disclosed paste also may have desirable mucoadhesion. In other words, the disclosed paste preferably will adhere or stick to the specific body tissue or passageway to which it is applied without having to fully pack the passageway to obtain adequate retention in the passageway. Desirably, the paste has an adhesive strength such that a separation force of about 5 grams to about 80 grams, about 20 to about 50 grams or about 15 to about 30 grams may be required. The separation force may be measured as the force required to separate two collagen-coated, rubber hemispheres compressed against one another with about a 4.4 Newton (1 pound) force using an MTS machine operated at a rate of 1 mm/s. The rubber hemispheres may be ultra soft Shore OO, 30 durometer black rubber with a diameter of about 5.08 cm (2 inches) and height of about 2.54 cm (1 inch) and a collagen coating to which about 0.2 to about 0.5 ml of the disclosed paste is desirably applied to the center of the lower hemisphere. Adhesion strength values are reported for sterilized paste. Desirably, the paste has a residence time in the applied passage or structure of at least 1 day, at least 3 days, at least 5 days, or at least 7 days with or without irrigation. The paste may degrade naturally or by irrigation (e.g. saline solution).

The disclosed paste desirably is non-cytotoxic with cytotoxicity scores of 0, 1 or 2 as measured by guidelines of ISO 10993-5, Biological Evaluation of Medical Devices-Part 5: Tests for in vitro Cytotoxicity. Desirably, the paste may have a cytotoxicity score of 1 or less.

The disclosed paste desirably is substantially collagen-free. Desirably the paste is sufficiently free of collagen (e.g., containing no collagen at all) so as to be saleable worldwide for use without restriction in humans. The disclosed paste desirably does not contain ingredients which might potentially harm mucosal tissues or structures, e.g., tissues in the nasal or sinus cavities.

The disclosed paste may be used as a part of a multi-step treatment regimen. For example, a series of steps that may be broadly classified as Cleansing/Disrupting, Killing, Aerating, Protecting/Coating, and Healing may be carried out. The Cleansing/Disrupting step may be carried out by administering a solvating system like those described in U.S. Pat. Nos. 7,976,873 B2 and 7,976,875 B2 and in U.S. Patent Application Publication No. 2011/0245757A1. The Killing step may be carried out by applying a suitable antimicrobial agent to the treatment site. This may for example be accomplished by including an antimicrobial agent in the solvating system, as a separately-applied agent, or in both the solvating system and as the separately-applied agent. An antimicrobial agent may also be applied or administered post operatively. The Aerating step may be carried out by providing air passageways or improving air passageways to the treated tissues by opening occluded or partially occluded passages, e.g., the sinuses or sinus ostia for nasal applications. This may for example be accomplished by surgically removing obstructive tissue structures or by manually displacing such structures. The Protecting/Coating step may be carried out by coating at least part of the thus-treated tissue with the disclosed paste. The Healing step may be carried out by allowing the cleansed, protected and sealed tissue surface to undergo a return to a normal state, e.g., through one or more healing mechanisms such as modulation of an inflammatory response, phagocytosis, mucosal remodeling, reciliation or full or partial restoration of normal function. The multi-step treatment regimen may include or be followed by a Clearing step in which the disclosed paste is sufficiently biodegradable to disappear from the treatment site in a desired time period, e.g., more than 5 days, or about 7 to 15 days or by irrigation. The paste desirably degrades or can be otherwise removed without shedding large solid chunks. The disclosed method may advantageously be accomplished without requiring surgery, for example by applying and removing the optional solvating system and by applying the disclosed paste through normal aspiration or suction techniques or by simple flushing of affected tissue.

The invention is further illustrated in the following non-limiting examples.

Example 1

Paste Formulations

A 3×PBS (pH 11-12) solution was prepared by dissolving PBS tablets in water and the pH was adjusted to pH 11-12 using 1N NaOH. Glycerol if used was then added to the PBS solution to form a PBS/Glycerol solution. To either the PBS solution or PBS/Glycerol solution were added varying amounts of dry ingredients, namely a 30-400 kDa molecular weight chitosan, glycerol phosphate disodium salt hydrate solid or polysaccharide and mixed at room temperature to form a paste. The paste was then gamma sterilized. All formulations except for formulation 4 formed a paste. Formulation 4 was initially liquid-like and subsequently became sticky and stringy. Table 1 shows the percentage of the ingredients in the total volume of liquid. Table 1 also shows the osmolality, viscosity and adhesion values for each formulation after sterilization.

| Formulation | Chitosan HCl (%) | Glycerol (% 1) | BGlyPh (%) | Polysaccharide (%) | Osmolality (mOSm/kg) | Sterile Viscosity (Pa·s) at Shear Rate 221 (1/s) | Average Sterile Adhesion Force (grams) |
|---|---|---|---|---|---|---|---|
| 1 | 13 | 0.6 | | | 2087 | 1.9 | 26.6 |
| 2 | 17 | 0.6 | | | 1730 | 3.2 | 26.4-37.7 |
| 3 | 17 | 0.6 | 6 | | 2882 | 4.9 | 38.3 |
| 4 | 8.5 | | 2 | dextran (20%) | 329 | 6.1 | 19.3 |
| 5 | 8.5 | | 2 | hydroxyethyl cellulose (2.5%) | 495 | NA | Less than 5 |
| 6 | 8.5 | | 2 | methyl cellulose (10%) | 557 | 10.5 | 39.5 |
| 7 | 8.5 | | 2 | hydroxypropyl cellulose (15%) | 177 | 8.2 | 33.1 |
| 8 | 13 | 0.6 | | hydroxypropyl cellulose (10%) | 1492-2048 | 13.8 | 44.4 |
| 9 | 13 | 0.6 | | hydroxypropyl cellulose (5%) | 2172 | 4.9 | 38.7 |
| 10 | 13 | 0.6 | | hydroxypropyl cellulose (1%) | 2048-2067 | 1.6 | 24.3 |

-continued

| Formulation | Chitosan HCl (%) | Glycerol (% 1) | BGlyPh (%) | Polysaccharide (%) | Osmolality (mOSm/kg) | Sterile Viscosity (Pa·s.) at Shear Rate 221 (l/s) | Average Sterile Adhesion Force (grams) |
|---|---|---|---|---|---|---|---|
| 11 | 17 | 0.6 | | hydroxypropyl cellulose (10%) | 2100 | 10.7 | 62.2 |
| 12 | 17 | 0.6 | | hydroxypropyl cellulose (5%) | 1787-1995 | 9.9 | 68.1 |
| 13 | 17 | 0.6 | | hydroxypropyl cellulose (1%) | 2083 | 3.5 | 35.4 |

Example 2

0.6 ml of 10% glycerol and 5.4 ml of 3×PBS solution (pH 11) as prepared in Example 1 were mixed in a 10 ml syringe. To this PBS/Glycerol solution was added varying amounts of glycerol phosphate, chitosan HCL and hydroxypropyl cellulose (HPC) in solid form. After all the ingredients in the syringe were fully mixed at room temperature, the resultant paste was gamma or E-beam sterilized. The formulations are shown below in Table 2. All the formulations formed a paste at room temperature. Table 2 shows the percentage of the various ingredients reported as a percentage of the total volume of liquid. The osmolality, viscosity and adhesion values for each formulation are shown below in Table 3 and are values after sterilization.

TABLE 2

| Formulation | Chitosan HCL (%) | HPC (%) | Glycerol Phosphate (%) |
|---|---|---|---|
| 14 | 8.5 | 3 | 1 |
| 15 | 13 | 4 | 2 |
| 16 | 10 | 3 | 1 |
| 17 | 10 | 3 | 1.5 |
| 18 | 13 | 2 | 2 |

TABLE 3

| Formulation | Osmolality (mOsm/kg) | Sterile Viscosity (Pa·s.) at Shear Rate 221 (l/s) Gamma | Sterile Viscosity (Pa·s.) at Shear Rate 221 (l/s) E-Beam | Sterile Adhesion Force (grams) Gamma | Sterile Adhesion Force (grams) E-Beam |
|---|---|---|---|---|---|
| 14 | Less than 1492 | 3 | 3.2 | 13.5 | 40.6 |
| 15 | Greater than or equal to 1492 | 1.7 | 0.4 | 14.5 | 45.5 |
| 16 | 525 | 1.8 | 2.3 | 22.8 | 65.0 |
| 17 | Less than 1492 | 1.6 | 1.4 | 17.4 | 67.3 |
| 18 | Greater than or equal to 1492 | 2.2 | 3.2 | 19.8 | 50.5 |

Example 3

Antimicrobial Properties

Formulations 14, 15 and 16 from Table 2 were evaluated to determine their antimicrobial activity against four common bacterial strains (*S. aureus, S. epidermis, E. coli* and *P. aeruginosa* using a zone of inhibition screening technique.

The four bacteria were grown on Muller Hinton agar plates. Under sterile conditions, approximately 0.1 to 0.2 ml of each formulation was directly placed on the agar plates. The agar plates were incubated at 35° C. for 12 hours. After incubation, the plates were observed for bacterial growth. The use of the term "zone of inhibition" denotes an area around the formulations where bacterial growth was inhibited. The term "bacteriostatic" denotes that the bacteria grew to the edge of the formulation but no further growth was observed. In other words, the term "bacteriostatic" refers to an ability to prevent bacteria from growing and multiplying but possibly not killing them.

The results shown in Table 4 below are based on triplicates per formulation.

TABLE 4

| Bacterial Strains | Zone of Inhibition or Bacteriostatic | | |
|---|---|---|---|
| | Formulation 14 | Formulation 15 | Formulation 16 |
| *S. aureus* | zone of inhibition | zone of inhibition | zone of inhibition |
| *S. epidermis* | zone of inhibition | zone of inhibition | zone of inhibition |
| *E. coli* | zone of inhibition | zone of inhibition | zone of inhibition |
| *P. aeruginosa* | bacteriostatic | bacteriostatic | bacteriostatic |

The results show that the formulations were antimicrobial and produced zones of inhibition.

Example 4

Cytotoxicity

Formulations 14 and 16 were either E-beam or gamma sterilized and were evaluated for potential cytotoxic effects following the guidelines of ISO 10993-5, Biological Evaluation of Medical Devices—Part 5: Tests for in vitro Cytotoxicity. Formulations 13 and 15 were extracted in purified water (PW) at 37° C. for 24 hours. The PW extract was mixed with double strength Minimum Essential Medium (2×MEM) to a 50% concentration. A negative control (high density polyethylene) and reagent control (e.g. PW) were similarly prepared. A positive control (powder-free latex gloves which include natural rubber latex, zinc carbamate accelerators, zinc oxide and titanium dioxide) was extracted in single strength MEM (1×MEM) at 37° C. for 24 hours. Triplicates of a mammalian cell culture monolayer having L-929 mouse fibroblast cells were dosed with each extract (formulations 14, 16, positive, negative and reagent controls) and incubated at 37° C. in the presence of 5% $CO_2$ for 48 hours. Following incubation, the monolayers were examined microscopically (100×) for abnormal cell morphology and cellular degeneration.

To confirm the scores, 0.2 ml of trypan blue stain was added to wells containing the test samples. The trypan blue molecule is large and cannot readily be absorbed by live cells. Only dead cells or those with compromised cell membranes take up the blue colored stain. Table 5 describes the scoring and visual characteristics.

TABLE 5

| Grade/Score | Reactivity | Conditions of all Cultures |
|---|---|---|
| 0 | None | Discrete intracytoplasmic granules, no cell lysis, no reduction of cell growth. |
| 1 | Slight | Not more than 20% of the cells are round, loosely attached and without intracytoplasmic granules, or show changes in morphology; occasional lysed cells are present; only slight growth inhibition observable. |
| 2 | Mild | Not more than 50% of the cells are round, devoid of intracytoplasmic granules; no extensive cell lysis; not more than 50% growth inhibition observable. |
| 3 | Moderate | Not more than 70% of the cell layers contain rounded cells or are lysed; cell layers not completely destroyed, but more than 50% growth inhibition observed. |
| 4 | Severe | Nearly complete or complete destruction of the cell layers. |

Below are the results for Formulations 14 and 16 that were either E-beam (e) or gamma (g) sterilized. The subscript e or g is used to denote the sterilization method.

TABLE 6

| Samples | Percent Rounding | Percent Cells Without Intracytoplasmic Granules | Percent Lysis | Grade | Reactivity |
|---|---|---|---|---|---|
| Formulation $14_e$ | 0 | 0 | 0 | 0 | None |
| Formulation $14_g$ | 0 | 0 | 0 | 0 | None |
| Formulation $16_e$ | 10 | 10 | 10 | 1 | Slight |
| Formulation $16_g$ | 0 | 0 | 0 | 0 | None |
| Negative Control | 0 | 0 | 0 | 0 | None |
| Reagent Control | 0 | 0 | 0 | 0 | None |
| Positive Control | Not Applicable | Not Applicable | 100 | 4 | Severe |

Formulation $16_e$ showed slight cell lysis or toxicity but is generally considered to be non-cytotoxic with a cytoxicity score of 1. Formulations $16_g$, $14_e$ and $14_g$ were shown to be nontoxic each having a cytoxicity score of 0.

Example 5

Ciliotoxicity in Rabbits

Formulations 14 and 16 were either E-beam or gamma sterilized and evaluated for their effect on rabbit cilia. A 0.6 cc portion of each formulation (Formulations 14, 16 and control (no treatment, saline only)) were applied to the bilateral maxillary sinus anstromies of randomized New Zealand White rabbits using a single lumen catheter. Following treatment, daily irrigation with 3 cc of saline was performed. At the end of 7 or 10 days, the rabbits were euthanized, and a piece of the medial wall of the maxillary sinuses was removed and fixed (Karnovsky's fixture) for scanning electron microscopy (SEM).

In a blind analysis, the tissues samples were evaluated and scored for the presence or absence of cilia. The results are shown in Table 7.

TABLE 7

| Formulation | E-beam | Gamma |
|---|---|---|
| Saline control | Cilia present | Cilia present |
| 14 | Cilia present | Cilia present |
| 16 | Cilia present | Cilia present |

Rabbits treated with the formulations showed the presence of cilia similar to the saline control. These results suggest that these formulations were non-toxic to cilia. In addition, the sterilization method did not appear to affect the formulation's toxicity towards cilia, namely both gamma and E-beam sterilized formulations were non-toxic to cilia.

Example 6

Ciliotoxicity in Sheep

Endoscopic sinus surgery including bilateral middle turbinectomy and partial thickness wounding around the ethmoidal cell was performed on sheep. The sheep were randomized and one nare was treated with 7 ml of each test formulation (formulation 7 and 8), the other nare with no treatment (control). Daily bilateral 20 cc saline irrigations were performed through the nose. Twenty-eight days after the surgery, two pieces of the medial wall of the nasal/sinus cavity were obtained from each sheep and each piece was fixed either for SEM analysis (Karnovsky's fixative) or histology or pathology evaluation (formalin). In a blind analysis, the tissue samples were evaluated and scored for the presence or absence of cilia.

No paste material was observed in the sheep after 28 days. SEM analysis showed cilia were present in both treated and control samples. Microscopic evaluation revealed similar inflammatory response between the treated samples and control. These results suggest that the formulations are safe for use in vivo.

Some additional non-limiting embodiments are provided below to further exemplify the present invention.

1. A paste in sterile packaging comprising a water-soluble chitosan, an osmolality reducing agent and a lubricating or wetting agent in a phosphate-containing solution to form a paste at a room temperature and having a pH of at least 4, wherein the osmolality reducing agent is not crosslinkable with the water-soluble chitosan and the paste has a viscosity of about 1 to about 15 Pa·s. and an osmolality of about 270 to about 2000 mOsm/kg, and the paste adheres to a tissue site and has a residence time of at least 1 day.
2. A sinus stent paste comprising a water-soluble chitosan, an osmolality reducing agent and a lubricating or wetting agent in a phosphate-containing solution, the paste forming at a room temperature and having a pH of at least 4, wherein the paste has a viscosity of about 1 to about 15 Pa·s., an osmolality of about 270 to about 2000 mOsm/kg and a residence time of at least 1 day and the osmolality reducing agent does not crosslink with the water-soluble chitosan.
3. A method for producing a paste comprising:
mixing a water-soluble chitosan, an osmolality reducing agent and a lubricating or wetting agent in a phosphate-containing solution to form a paste at room temperature and having a pH of at least 4, wherein the paste has a viscosity of about 1 to about 15 Pa·s., an osmolality of about 270 to about 2000 mOsm/kg and a residence time of at least 1 day and the osmolality reducing agent does not crosslink with the water-soluble chitosan.
4. The embodiment 1, 2 or 3 wherein the water-soluble chitosan comprises a salt.
5. The embodiment 1, 2 or 3 wherein the water-soluble chitosan comprises a hydrochloric acid salt.
6. The embodiment 1, 2 or 3 wherein the water-soluble chitosan is about 3-20 wt. % of total paste weight.
7. The embodiment 1, 2 or 3 wherein the osmolality reducing agent comprises an alkyl or hydroxyl functional cellulose.
8. The embodiment 7 wherein the alkyl or hydroxyl functional cellulose is hydroxypropyl cellulose, methyl cellulose or hydroxyethyl cellulose.
9. The embodiment 1, 2 or 3 wherein the lubricating or wetting agent comprises glycerol.
10. The embodiment 1, 2 or 3 wherein the phosphate containing solution is a phosphate buffered saline (PBS).
11. The embodiment 1, 2, 3 or 10 wherein the phosphate-containing solution is a 3×PBS solution.
12. The embodiment 1, 2, 3 or 11 wherein the phosphate containing solution has a pH between 9 and 12.
13. The embodiment 1 wherein the sterile packaging is electron-beam or gamma sterilized.
14. The embodiment 13 wherein the sterilization energy is between about 12 to about 40 kGy.
15. The embodiment 1, 2 or 3 wherein the residence time is at least 3 days.
16. The embodiment 1, 2 or 3 having an adhesive strength of between about 5 grams and about 80 grams of force required to separate two collagen coated hemispheres coated with the paste that have been compressed against one another with about a 4.4 Newton force using an MTS machine operated at a rate of about 1 mm/s.
17. The embodiment 1, 2 or 3 that is non-cytotoxic.
18. The embodiment 17 having a cytotoxicity score of 1 or less.
19. The embodiments 1, 2 or 3 further comprising glycerol phosphate.
20. A stent or packing formed from the composition of embodiment 1.
21. The stent of embodiment 20 wherein the stent or packing contacts nasal or sinus passage.

All patents, patent applications and literature cited in the specification are hereby incorporated by reference in their entirety. In the case of any inconsistencies, the present disclosure, including any definitions therein will prevail. Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

We claim:

1. A sinus stent paste comprising a water-soluble chitosan or derivative thereof and an osmolality reducing agent in a phosphate-containing solution to provide an opaque paste at room temperature containing at least 5 wt. % of the water-soluble chitosan or derivative thereof based on the total paste weight and having a pH of at least 4, a viscosity of about 1 to about 15 Pa·s., an osmolality of about 270 to about 2000 mOsm/kg, and a residence time of at least 1 day, wherein the osmolality reducing agent does not crosslink with the water-soluble chitosan.

2. The paste according to claim 1 wherein the water-soluble chitosan comprises a hydrochloric acid salt.

3. The paste according to claim 1 wherein the water-soluble chitosan or derivative thereof is up to about 20 wt % of the total paste weight.

4. The paste according to claim 1 wherein the water-soluble chitosan or derivative thereof is about 12 wt. % to about 18 wt. % of the total paste weight.

5. The paste according to claim 1 wherein the osmolality reducing agent is an alkyl or hydroxyl functional cellulose.

6. The paste according to claim 5 wherein the alkyl or hydroxyl cellulose is hydroxypropyl cellulose, methyl cellulose or hydroxyethyl cellulose.

7. The paste according to claim 1 wherein the osmolality reducing agent is about 1 to about 20 wt % of the total paste weight.

8. The paste according to claim 1 wherein the phosphate-containing solution is a phosphate buffered saline having a pH between 9 and 12.

9. The paste according to claim 1 in sterilized packaging.

10. The paste according to claim 9 wherein the sterilization is electron-beam radiation or gamma radiation.

11. The paste according to claim 1 having an adhesive strength of between about 5 grams and about 80 grams of force required to separate two collagen coated hemispheres to which the paste is applied and compressed against one another with about 4.4 Newton force using an MTS machine operated at a rate of 1 mm/s.

12. The paste according to claim 1 wherein the paste is non-cytotoxic with a cytotoxicity score of 1 or less.

13. The paste according to claim 1 wherein the phosphate-containing solution is a glycerol phosphate.

14. The paste according to claim 1 further comprising a lubricant or wetting agent.

15. The paste according to claim 14 wherein the lubricant or wetting agent is glycerol.

16. The paste according to claim 14 wherein the lubricant or wetting agent is about 1 about 10 wt % of the total paste weight.

17. The paste according to claim 1 further packaged as ready-to-use composition.

18. A method of preparing a chitosan stenting paste comprising the steps of:
mixing a water-soluble chitosan or derivative thereof and an osmolality reducing agent in a phosphate-containing solution to provide an opaque paste at room temperature containing at least 5 wt. % of the water-soluble chitosan or derivative thereof based on the total paste weight and having a pH of at least 4, a viscosity of about 1 to about 15 Pa·s., an osmolality of about 270 to about 2000 mOsm/kg, and a residence time of at least 1 day wherein the osmolality reducing agent does not crosslink with the water-soluble chitosan.

19. A method of stenting comprising:
a) providing a composition comprising a water-soluble chitosan or derivative thereof and an osmolality reducing agent in a phosphate-containing solution to provide an opaque paste at room temperature containing at least 5 wt. % of the water-soluble chitosan or derivative thereof based on the total paste weight and having a pH of at least 4, a viscosity of about 1 to about 15 Pa·s., and an osmolality of about 270 to about 2000 mOsm/kg, wherein the osmolality reducing agent does not crosslink with the water-soluble chitosan; and
b) applying the paste onto a nasal or sinus site to form a protective packing, layer or stent wherein the paste adheres to the nasal or sinus site and has a residence time of at least 1 day.

20. The method according to claim 19 wherein the method further comprises irrigating the applied paste at the nasal or sinus site.

\* \* \* \* \*